United States Patent [19]
Kanai et al.

[11] Patent Number: 5,905,174
[45] Date of Patent: May 18, 1999

[54] METHOD FOR PRODUCING 3,3-DICHLORO-1,1,1-TRIFLOUROACETONE

[75] Inventors: Masatomi Kanai; Takashi Sakaya; Mineo Watanabe; Yoshihiko Goto; Ryo Nadano, all of Saitama, Japan

[73] Assignee: Central Glass Company, Limited, Yamaguchi, Japan

[21] Appl. No.: 09/060,180

[22] Filed: Apr. 15, 1998

[30] Foreign Application Priority Data

Apr. 15, 1997 [JP] Japan .................................... 9-097623
Apr. 15, 1997 [JP] Japan .................................... 9-097624
May 28, 1997 [JP] Japan .................................... 9-137376

[51] Int. Cl.$^6$ .................................................. C07C 45/00
[52] U.S. Cl. .......................... 568/411; 568/383; 568/407; 568/419
[58] Field of Search .................... 568/383, 403, 568/404, 406, 407, 411, 419

[56] References Cited

FOREIGN PATENT DOCUMENTS 9-227440  9/1997  Japan .

OTHER PUBLICATIONS

Yu Zeifman et al., "Polyfluorinated Al–Enolates," *Doklady Akademii Nauk USSR* (English Translation), vol. 307, No. 6, Aug. 1989, pp. 241–245.

J. Fernandez–Bolaños et al., "The Synthesis of 4, 5–bistrifluoromethylbenzimidazole," *Journal of the Chemical Society*, vol. 1960, 1960, pp. 4003–4010.

*Primary Examiner*—Gary Geist
*Assistant Examiner*—Sreeni Padmanabhan
*Attorney, Agent, or Firm*—Evenson, McKeown Edwards & Lenahan P.L.L.C.

[57] ABSTRACT

The invention relates to a method for producing 3,3-dichloro-1,1,1-trifluoroacetone. This method includes a step of fluorinating pentachloroacetone by hydrogen fluoride in the presence of a fluorination catalyst. This fluorination may be conducted in a liquid phase in the presence of an antimony compound as the fluorination catalyst. Alternatively, the fluorination may be conducted in a gas phase in the presence of a fluorination catalyst which may be a fluorinated alumina or at least one compound of at least one metal selected from Al, Cr, Mn, Ni, and Co. The method is suited to an industrial scale production of 3,3-dichloro-1,1,1-trifluoroacetone. The invention further relates to another method for producing 3,3-dichloro-1,1,1-trifluoroacetone. This method includes a step of purifying a crude 3,3-dichloro-1,1,1-trifluoroacetone by a distillation in the presence of water, thereby to produce 3,3-dichloro-1,1,1-trifluoroacetone which is substantially free of organic matters other than 3,3-dichloro-1,1,1-trifluoroacetone. This crude 3,3-dichloro-1,1,1-trifluoroacetone may be the reaction products of the fluorination of pentachloroacetone in a gas phase. Due to the provision of the another method, 3,3-dichloro-1,1,1-trifluoroacetone can be produced with high yield.

31 Claims, No Drawings

METHOD FOR PRODUCING 3,3-DICHLORO-1,1,1-TRIFLOUROACETONE

BACKGROUND OF THE INVENTION

The present invention relates to a method for producing 3,3-dichloro-1,1,1-trifluoroacetone which is useful as an intermediate of medicines and agricultural chemicals and as a reagent for introducing fluorine-containing groups.

English translation (pp. 241–245) of Doklady Akademii Nauk SSSR, Vol. 307, No. 6, pp. 1385–1390, August, 1989 discloses that 3,3-dichloro-1,1,1-trifluoroacetone is synthesized from 3,3,3-trichloro-1,1,1-trifluoropropane-2-one in an anhydrous solvent, through an Al-enolate intermediate, using a mercury compound catalyst. In this synthesis, it is necessary to strictly maintain the reaction system under an anhydrous condition and use a mercury compound catalyst which is hazardous. Thus, this synthesis is not suited to an industrial scale production of 3,3-dichloro-1,1,1-trifluoroacetone. In view of this, there is a demand for a method for producing 3,3-dichloro-1,1,1-trifluoroacetone, which is suited to an industrial scale production therefor.

Japanese Patent Unexamined Publication JP-A-9-227440 discloses another method for producing 3,3-dichloro-1,1,1-trifluoroacetone by chlorinating a trifluoroacetoacetate represented by the formula $CF_3COCH_2CO_2R$, where R is a lower alkyl group, and then decarboxylating the chlorinated trifluoroacetoacetate.

SUMMARY OF THE INVENTION

It is an object of the present invention to provide a method for producing 3,3-dichloro-1,1,1-trifluoroacetone, which is suited to an industrial scale production therefor.

It is another object of the present invention to provide a method for producing 3,3-dichloro-1,1,1-trifluoroacetone with a high yield.

According to a first aspect of the present invention, there is provided a method for producing 3,3-dichloro-1,1,1-trifluoroacetone. This method comprises a step of fluorinating pentachloroacetone by hydrogen fluoride in the presence of a fluorination catalyst. The method may be a first method comprising a step of fluorinating pentachloroacetone by hydrogen fluoride in a liquid phase in the presence of an antimony compound as the fluorination catalyst The inventors unexpectedly found that 3,3-dichloro-1,1,1-trifluoroacetone can be obtained with a high yield by using an antimony compound in the fluorination of pentachloroacetone in a liquid phase. Alternatively, the method may be a second method comprising a step of fluorinating pentachloroacetone by hydrogen fluoride in a gas phase in the presence of a fluorination catalyst. The inventors unexpectedly found that 3,3-dichloro-1,1,1-trifluoroacetone can continuously easily be obtained by using a fluorination catalyst (e.g., fluorinated alumina) in the fluorination of pentachloroacetone in a gas phase. As will be clarified hereinafter, the reaction products of the first or second method may be purified by the following third method.

According to a second aspect of the present invention, there is provided a third method for producing 3,3-dichloro-1,1,1-trifluoroacetone. The third method comprises a step of purifying a crude 3,3-dichloro-1,1,1-trifluoroacetone by a distillation in the presence of water, thereby to produce 3,3-dichloro-1,1,1-trifluoroacetone which is substantially free of organic matters other than 3,3-dichloro-1,1,1-trifluoroacetone. As mentioned above, the crude 3,3-dichloro-1,1,1-trifluoroacetone used in the third method may be the reaction products of the first or second method. In fact, depending on the reaction conditions, the reaction products of the second method may contain fluorochlorinated acetones (e.g., 3-chloro-1,1,1-trifluoroacetone, 3,3,3-trichloro-1,1,1,-trifluoroacetone, and 1,3,3-trichloro-1,1-difluoroacetone) besides 3,3-dichloro-1,1,1-trifluoroacetone (boiling point: 75° C). In particular, 3-chloro-1,1,1-trifluoroacetone (boiling point: 70° C.) and 3,3,3-trichloro-1,1,1-trifluoroacetone (boiling point: 85° C.) are each near to 3,3-dichloro-1,1,1-trifluoroacetone in boiling point, and thus it is very difficult to separate 3,3-dichloro-1,1,1-trifluoroacetone from these compounds by an ordinary distillation. In view of this, the inventors have eagerly examined the purification of 3,3-dichloro-1,1,1-trifluoroacetone, and unexpectedly found that 3,3-dichloro-1,1,1-trifluoroacetone can easily be purified by distilling the crude 3,3-dichloro-1,1,1-trifluoroacetone in the presence of water. With this, 3,3-dichloro-1,1,1-trifluoroacetone is efficiently separated from chlorofluorinated acetone by-products, such as 3-chloro-1,1,1-trifluoroacetone and 3,3,3-trichloro-1,1,1-trifluoroacetone.

DESCRIPTION OF THE PREFERRED EMBODIMENTS

Pentachloroacetone, which is used in the above-mentioned first or second method of the present invention, can be synthesized by a conventional method. For example, it can be synthesized by chlorinating acetone by chlorine in the presence of a catalyst (e.g., light, metal chlorides, acids and metal salts of organic acids). Furthermore, it can be synthesized by oxidizing a chlorinated alcohol.

It is known to use an antimony catalyst for fluorinating halogenated hydrocarbons in a liquid phase by hydrogen fluoride. It is generally assumed that this antimony catalyst under its activated condition during the fluorination takes a form of a halogenated antimony compound represented by a formula of $SbF_aX_b$ where X is a halogen, "a" and "b" are numbers each ranging from 0 to 5, and the total of "a" and "b" equals to 5. Thus, it is assumed that an antimony compound used as the fluorination catalyst in the first method also takes a form of such halogenated antimony compound, regardless of the form of the original antimony compound, when the antimony compound is under its activated condition during the fluorination. A halogenated antimony(III) compound, which is in a non-activated condition, is easily oxidized to another halogenated antimony(V) compound, which is in an activated condition, by chlorine, bromine or fluorine. Therefore, an antimony compound that is introduced as a catalyst into the reaction system of the first method is not limited to an antimony(V) compound. Examples of an antimony compound used in the first method are antimony pentachloride, antimony pentabromide, antimony pentaiodide, antimony pentafluoride, antimony trichloride, antimony tribromide, antimony triiodide, and antimony trifluoride. Of these, antimony pentachloride and antimony trichloride are particularly preferable examples In the first method, the fluorination catalyst is in an amount of preferably from 0.1 to 50 moles, more preferably from 1 to 20 moles, still more preferably from 5 to 10 moles, per 100 moles of pentachloroacetone. If it is less than 0.1 moles, both of conversion of pentachloroacetone and yield of 3,3-dichloro-1,1,1-trifluoroacetone may become too low. If it is greater than 50 moles, tarry substances made up of high-boiling-point compounds and/or excessively fluorinated reaction products may be produced too much.

In the first method, the reaction temperature is preferably from 30 to 200° C., more preferably from 50 to 150° C., still more preferably from 80 to 120° C. If it is lower than 30° C., both of conversion of pentachloroacetone and yield of 3,3-dichloro-1,1,1-trifluoroacetone may become too low. If it is higher than 200° C., tarry substances and/or excessively fluorinated reaction products may be produced too much.

In the first method, the molar ratio of hydrogen fluoride to pentachloroacetone is preferably from 2:1 to 50:1, more preferably from 3:1 to 20:1, still more preferably from 5:1 to 10:1. If it is less than 2:1, conversion of pentachloroacetone may not become sufficiently high. If it is greater than 50:1, conversion of pentachloroacetone may not improve further, as compared with a case in which it is within this range of from 2:1 to 50:1. Furthermore, this may not economically be advantageous from the viewpoint of the recovery of the unreacted hydrogen fluoride.

In the first method, pressure needed to conduct the fluorination varies depending on the reaction temperature, and this pressure is not particularly limited as long as the reaction mixture in the reactor is maintained in the form of liquid. The pressure is preferably from 1.0 to 100 kg/cm$^2$, more preferably from 5 to 30 kg/cm$^2$.

In the first method, a solvent may be added to the reaction system in order to adjust the reaction rate and to suppress deterioration of the fluorination catalyst. Preferable examples of this solvent are 1,3-bistrifluoromethylbenzene and 2,4-dichloro-1-trifluoromethylbenzene, which are hardly further fluorinated or chlorinated.

When the fluorination catalyst of the first method has deteriorated or has been an antimony compound that has an antimony's oxidation number other than +5, this fluorination catalyst can easily be activated to an activated condition where its antimony has an oxidation number of +5. This activation may be conducted by introducing chlorine at a temperature of from 10 to 150° C., in the presence of pentachloroacetone, 3,3-dichloro-1,1,1-trifluoroacetone or the above-mentioned solvent. Alternatively, the activation may be conducted by introducing chlorine continuously or intermittently into the reaction system of the fluorination of pentachloroacetone. Upon or after the introduction, stirring is conducted, if necessary. For the activation, chlorine is used in an amount of from 1 to 100 moles per mol of the catalyst. If the temperature is lower than 10° C., it takes too long time to achieve the activation. If it is higher than 150° C., the coexisting pentachloroacetone, 3,3-dichloro-1,1,1-trifluoroacetone and/or the above-mentioned solvent may be chlorinated.

In the first method, the fluorination may be conducted by a continuous operation, a batch operation, or a half-batch operation in which only the reaction product (hydrogen chloride) is continuously removed from a reactor. Depending on the manner of the operation, it is optional to modify the reaction condition(s).

A reactor used in the first method is preferably made of a material such as Hastelloy, stainless steel, Monel metal or nickel, or a material lined with one of these metals, tetrafluoroethylene resin, chlorotrifluoroethylene resin, vinylidene fluoride resin or PFA resin.

In each of the first and second methods, the obtained 3,3-dichloro-1,1,1-trifluoroacetone may be purified by a conventional method for purifying reaction products obtained by the fluorination. In this purification, for example, 3,3-dichloro-1,1,1-trifluoroacetone, together with hydrogen chloride and the unreacted hydrogen fluoride, is discharged in the form of liquid or gas, from a reactor. Then, hydrogen chloride and an excessive amount of hydrogen fluoride are removed from the discharge by distillation, the liquid phase separation or the like. Then, an acid component is removed therefrom using a basic solution or the like. After that, the aimed 3,3-dichloro-1,1,1-trifluoroacetone having a high purity is obtained by rectification. Alternatively, the reaction products of the first or second method may be purified by the third method of the present invention, as mentioned hereinabove.

In the second method, the fluorination catalyst may be a fluorinated alumina prepared by fluorinating an alumina. This fluorinated alumina according to the invention is defined as an alumina that has been fluorinated with varying degrees, and thus it may be an aluminum fluoride, an aluminum oxyfluoride, or a hydroxyl-containing aluminum oxyfluoride. An alumina used for preparing the fluorinated alumina is not particularly limited and may be one obtained by molding and drying an aluminum hydroxide precipitate formed from an aluminum salt aqueous solution by using ammonia or the like. A commercial τ-alumina, which is used as a catalyst carrier or a drying agent, is preferably used in the second method. It is preferable that the fluorinated alumina is prepared by partially or completely fluorinating an alumina with a fluorine-containing substance. Examples of this fluorine-containing substance are inorganic fluorination agents, such as hydrogen fluoride, ammonium fluoride, fluorine, chlorine monofluoride, chlorine trifluoride, sulfur hexafluoride and nitrogen trifluoride, and organic fluorination agents, such as chlorodifluoromethane, difluoromethane, trifluoromethane, carbon tetrafluoride, hexafluoroethane, 1,1,1,2-tetrafluoroethane and pentafluoroethane.

In the second method, the method of fluorinating an alumina with a fluorine-containing substance for producing the fluorinated alumina is not particularly limited. For example, an alumina may be immersed in a hydrogen fluoride solution (e.g., hydrogen fluoride aqueous solution), followed by drying of the immersed alumina. As another example, a hydrogen fluoride solution may be sprayed onto an alumina, followed by drying. As a further example, an alumina introduced into a container is heated, and then the above-mentioned fluorine-containing substance is allowed to flow through this container. In the final step of the production of the fluorinated alumina, it is preferable to bring hydrogen fluoride into contact with an alumina at a temperature (preferably from 200 to 500° C., more preferably from 250 to 450° C.,) that is not lower than the temperature of the fluorination of pentachloroacetone.

In the second method, the fluorination catalyst may be at least one compound of at least one metal selected from the group consisting of aluminum, chromium, manganese, nickel, cobalt, and iron. When a combination of at least two compounds of at least two metals is used for preparing the fluorination catalyst, it is preferable that one metal of the at least two metals is aluminum, chromium, or iron. Examples of the at least one compound of the fluorination catalyst are oxide, fluoride, chloride, fluorochloride, oxyfluoride, oxychloride, and oxyfluorochloride. The at least one compound may be carried on a carrier such as an aluminum compound or activated carbon. Examples of this aluminum compound are aluminum oxide, fluoride, chloride, fluorochloride, oxyfluoride, oxychloride, and oxyfluorochloride.

In the second method, the manner of preparing the fluorination catalyst, which is the above-mentioned at least one compound of the at least one metal, is not particularly limited. When the at least one compound is not carried on a carrier, the at least one compound may be prepared, as follows. At first, a metal hydroxide is precipitated from a solution of a compound of the at least one metal, using a basic substance. After that, this metal hydroxide is turned into a metal oxide, and then this metal oxide is partially or completely modified by halogen, using hydrogen fluoride, hydrogen chloride, chlorofluorohydrocarbon, and the like. In contrast, when the at least one compound is carried on a carrier, the carrier may be immersed into a solution of the at least one compound, or alternatively this solution may be sprayed on the carrier. After that, the carrier is dried and then partially or completely fluorinated by the above-mentioned fluorine-containing substance. The carrier may be, for example, an aluminum oxide such as τ-alumina or an alumina that has previously been modified by hydrogen fluoride, hydrogen chloride, chlorofluorohydrocarbon or the like.

In the second method, the amount of the at least one metal of the fluorination catalyst is preferably from 0.1 to 100 parts by weight, more preferably from 1 to 50 parts by weight, per 100 parts by weight of the carrier. It is optional to add an additive that is at least one element of alkali-earth metals such as Mg and Ca and lanthanide series elements such as La and Ce, to the fluorination catalyst. This additive prevents recrystallization of an oxyhalide used as the at least one metal or as the carrier, thereby maintaining activity of the fluorination catalyst. The weight ratio of the at least one metal to the additive is preferably from 50:50 to 99.9:0.1 and more preferably from 70:30 to 99:1.

In the second method, the at least one metal compound used for preparing the fluorination catalyst may be at least one of nitrate, chloride, oxide and the like of the at least one metal, which is soluble in a solvent such as water, ethanol, or acetone. Examples of the at least one metal compound are chromium nitrate, chromium trichloride, chromium trioxide, potassium dichromate, manganese nitrate, manganese chloride, manganese dioxide, nickel nitrate, nickel chloride, cobalt nitrate, cobalt chloride, iron nitrate, and iron chloride. These compounds may be in the form of hydrate, and metals of these compound are not particularly limited in valence.

In the second method, compositional change of the fluorination catalyst during the fluorination of pentachloroacetone can effectively be prevented by treating, prior to the fluorination, the fluorination catalyst with a fluorination agent such as hydrogen fluoride, fluorohydrocarbon or fluorochlorohydrocarbon, at a temperature not lower than the reaction temperature of the fluorination. The fluorination catalyst can effectively be prolonged in lifetime, and furthermore conversion and yield of the fluorination can effectively be improved, by supplying the reactor with oxygen, chlorine, fluorohydrocarbon or fluorochlorohydrocarbon, during the fluorination.

In the second method, once the fluorination catalyst is inactivated by the fluorination, the fluorination catalyst can easily be reactivated. In other words, the inactivated catalyst can be reactivated by contact with an oxidative substance (e.g., oxygen, air, ozone, and chlorine) at a temperature of from 200 to 550° C., preferably from 300 to 500° C. If the temperature is lower than 200° C., it becomes difficult to reactivate the catalyst. If it is higher than 550° C., the catalyst is deteriorated.

In the second method, the temperature of the fluorination of pentachloroacetone is preferably from 150 to 500° C., more preferably from 180 to 400° C., still more preferably from 200 to 300° C. If it is lower than 150° C., the reaction rate may become impractically slow. If the temperature is too high, the reaction rate becomes high. With this, however, there may be produced an excessively fluorinated compound such as pentafluoroacetone, and thus selectivity of 3,3-dichloro-1,1,1-trifluoroacetone may be lowered. Furthermore, the catalyst may become too short in lifetime.

In the second method, the ratio by mol of pentachloroacetone to hydrogen fluoride varies depending on the reaction temperature. This ratio is preferably from 1:50 to 1:3, more preferably from 1:20 to 1:4, still more preferably from 1:15 to 1:5. In order to obtain a high reaction rate, it is preferred that the concentration of hydrogen fluoride is high in the reaction system, because it is assumed that an equilibrium state exists among 3,3-dichloro-1,1,1-trifluoroacetone, its precursors, hydrogen fluoride and hydrogen chloride. If the amount of hydrogen fluoride is too large in the second method, the amount of the reaction product contained in the unit volume of the gas released from the reactor may become small. Furthermore, it may become difficult to separate the reaction product from a mixture of the reaction products and the unreacted hydrogen fluoride released from the reactor. If the amount of hydrogen fluoride is too small in the second method, conversion may become low, thereby lowering yield of the reaction product. However, even if the amount of hydrogen fluoride is too much or too little in the second method, that is not critical to the fluorination of a large scale, because low-fluorinated compounds, unreacted substances, and/or hydrogen fluoride, which usually accompanies the reaction product, is separated from the reaction product and is reused.

In the second method, the reaction pressure is not particularly limited. It is preferably from 1 to 10 $kg/cm^2$ from the viewpoint of the selection of the reactor material. It is preferable to select a reaction condition in which pentachloroacetone, intermediate products and hydrogen fluoride, which exist in the reaction system, are not liquefied in the reaction system. The contact time of the fluorination is preferably from 0.1 to 300 seconds, more preferably from 1 to 60 seconds, still more preferably from 10 to 30 seconds The reactor's material used in the second method is not particularly limited, as long as the reactor has a sufficient heat resistance and a sufficient corrosion resistance against hydrogen fluoride, hydrogen chloride and the like. It is preferably stainless steel, Hastelloy, Monel metal or platinum, or a material lined with one of these metals.

As mentioned above, a crude 3,3-dichloro-1,1,1-trifluoroacetone used in the third method may be the reaction products of the second method. The method for producing this crude 3,3-dichloro-1,1,1-trifluoroacetone is, however, not particularly limited. The crude 3,3-dichloro-1,1,1-trifluoroacetone may vary in the types and the contents of impurities thereof, depending on the manner of producing the same. The third method of the present invention is not particularly limited by the variation of the types and the contents of impurities of the crude 3,3-dichloro-1,1,1-trifluoroacetone. In case that the reaction products of the second method are used as the crude 3,3-dichloro-1,1,1-trifluoroacetone of the third method, it is preferable to remove an acid component (e.g., hydrogen fluoride and hydrogen chloride) from the crude 3,3-dichloro-1,1,1-trifluoroacetone, prior to the distillation of the third method. Furthermore, it is more preferable to remove therefrom certain components that have boiling points relatively remote from that of 3,3-dichloro-1,1,1-trifluoroacetone by a simple distillation (e.g., flash distillation), prior to the distillation of the third method. In particular, it is preferable to remove therefrom chlorofluoroacetones having five halogen atoms and one hydrogen atom in the molecule, prior to the distillation of the third method.

The distillation of the third method may be conducted by a continuous operation, a batch operation, or a half-batch operation by using a conventional facility. The type of the distillation tower is not particularly limited in the third method, and may be a packed tower, a plate tower or a bubble-cap tower. In the third method, water to be added to the crude 3,3-dichloro-1,1,1-trifluoroacetone is in an amount of preferably at least 2 moles per mol of 3,3-dichloro-1,1, 1-trifluoroacetone contained in the crude 3,3-dichloro-1,1, 1trifluoroacetone. The upper limit of the amount of this water is not particularly limited and may be about 5 moles per mol thereof. The manner of conducting the distillation of the third method may be a conventional one.

As stated above, a flash distillation (preliminary distillation) may previously be conducted to remove chlorofluoroacetones other than 3-chloro-1,1,1-trifluoroacetone and 3,3,3-trichloro-1,1,1-trifluoroacetone, from the crude 3,3-dichloro-,1,1,1-trifluoroacetone. Then, the resultant crude 3,3-dichloro-1,1,1-trifluoroacetone may be subjected to the distillation of the third method. During this distillation, 3-chloro-1,1,1-trifluoroacetone firstly distills out. Then, a component containing 3,3-dichloro-1,1,1-trifluoroacetone distills out at from 103 to 105° C. under a pressure of 1 kg/cm$^2$, preferably at about 103.5° C. At this time, 3,3-dichloro-1,1,1-trifluoroacetone that is substantially free of other organic matters is trapped in a receiver, together with water in an amount of about 2 moles per mol of 3,3-dichloro-1,1,1-trifluoroacetone. This 3,3-dichloro-1,1,1-trifluoroacetone trapped in the receiver may take a form of 3,3-dichloro-1,1,1-trifluoroacetone dihydrate or 3,3-dichloro-1,1,1-trifluoropropane-2,2-diol monohydrate. The distillation of the third method is not particularly limited by which form 3,3-dichloro-1,1,1-trifluoroacetone takes, that is, 3,3dichloro-1,1,1-trifluoroacetone dihydrate, 3,3-dichloro-1,1,1-trifluoropropane-2,2-diol monohydrate, or a hydrate having any number of water molecule. When the distillation of the third method is conducted, it is optional to add calcium chloride or boric acid to the distillation still. Water can be removed from the 3,3-dichloro-1,1,1-trifluoroacetone obtained in the third method by a conventional manner. For example, water can easily be removed therefrom by contact with a drying agent (e.g., concentrated sulfuric acid, phosphoric acid or phosphoric anhydride) at a temperature of from about 25 to 150° C., thereby to obtain 3,3-dichloro-1,1,1-trifluoroacetone that is free of water. It should be noted that a hydrate of 3,3-dichloro-1,1,1-trifluoroacetone also has advantageous uses similar to those of 3,3-dichloro-1,1,1-trifluoroacetone.

The following nonlimitative Example 1 is illustrative of the first aspect of the present invention.

EXAMPLE 1

In this example, 3,3-dichloro-1,1,1-trifluoroacetone was prepared from pentachloroacetone, as follows, in accordance with the first method of the present invention.

At first, a 10-liter autoclave made of stainless steel (SUS 316L) and equipped with a reflux condenser and a stirrer was charged with 420 g of antimony pentachloride (catalyst) and 3,500 g of hydrogen fluoride. Then, stirring of the resultant mixture was started at room temperature (about 15° C). After a lapse of 30 minutes, 5,400 g of pentachloroacetone was pressed into the autoclave, when the autoclave's inside pressure increased to 3 kg/cm$^2$ due to the generation of hydrogen chloride. Then, the temperature of the heating medium of the autoclave was increased. With this, autoclave's inside temperature reached about 80° C., and hydrogen chloride was vigorously generated. When the autoclave's inside pressure reached 13 kg/cm$^2$, it was started to remove hydrogen chloride from the autoclave through the reflux condenser in order to maintain the reaction pressure at 13 kg/cm$^2$ during the reaction. Six hours after the beginning of the reaction, the generation of hydrogen chloride terminated, and the autoclave's inside pressure started to decrease. Upon this, the autoclave was cooled down, and at the same time the pressure was decreased to atmospheric pressure. After cooling of the autoclave, hydrogen fluoride was removed from the autoclave by distillation by adjusting the temperature of the reflux condenser to 20° C. and by increasing the autoclave's inside temperature to 50° C. Then, the temperature of the heating medium of the autoclave was increased to 120° C. Under this condition, a flash distillation was conducted, while the effluent was not allowed to flow through the reflux condenser. With this, 2,650 g of an organic matter was obtained. By analysis with a gas chromatograph, it was found that this organic matter contains 70.2 wt % of 3,3-dichloro-1,1,1-trifluoroacetone, 8.5 wt % of 1-chloro-1,3,3,3-tetrafluoroacetone, 3.5 wt % of 1,3-dichloro-1,1,3-trifluoroacetone, 10.4 wt % of 1,3,3-trichloro-1,1-difluoroacetone, and other substances.

The following nonlimitative Examples 2–5 are illustrative of the first aspect of the present invention. In these examples, 3,3-dichloro-1,1,1-trifluoroacetone was prepared from pentachloroacetone, as follows, in accordance with the second method of the present invention.

EXAMPLE 2

In this example, the fluorination catalyst was prepared as follows. At first, 400 g of an activated alumina having a particle diameter of from 4 to 6 mm, KHS-46 (trade name) of SUMITOMO CHEMICAL CO., LTD., was washed with water to remove a powder attached to the surface of the activated alumina. Separately, 10% hydrofluoric acid solution was prepared by dissolving 153 g of anhydrous hydrogen fluoride into 1,380 g of water. Then, the hydrofluoric acid solution was gradually poured on the activated alumina. After stirring, this mixture was allowed to stand still for 3 hr. After that, the activated alumina separated from the solution was washed with water, then was separated from water by filtration, and then was dried at 200° C. for 2 hr in an electric furnace. Then, 400 cc of the dried activated alumina was put into a stainless steel reaction tube having an inner diameter of 4.2 cm and an axial length of 60 cm. Then, this reaction tube was put into the electric furnace, and then the electric furnace temperature was increased to 200° C., while nitrogen gas was allowed to flow through the reaction tube. After that, hydrogen fluoride gas together with nitrogen gas was allowed to flow therethrough to treat the activated aluminum with hydrogen fluoride. As this treatment proceeded, the catalyst temperature increased. In this treatment, flow rates of nitrogen and hydrogen fluoride were respectively adjusted such that the catalyst temperature did not exceed 400° C. After this exothermic reaction of the activated aluminum with hydrogen fluoride has finished, the reaction tube was further kept in the electric furnace at 400° C., for 2 hr to prepare the fluorination catalyst.

Then, a cylindrical reaction tube for conducting a gas phase reaction was charged with 400 g of the obtained fluorination catalyst. This reaction tube was equipped with an electric furnace and was made of stainless steel (SUS316L) and had a diameter of 4.2 cm and an axial length of 60 cm. The reaction tube temperature was increased to 250° C., while nitrogen gas was allowed to flow therethrough at a flow rate of about 1.2 liter per hour. Then, hydrogen fluoride gas was allowed to flow therethrough at a flow rate of about 36 g/hr, together with nitrogen gas. Under this condition, the reaction tube temperature was increased to 300° C. and then maintained at this temperature for 1 hr. Then, the reaction tube temperature was lowered to 250° C., and then the reaction (fluorination) was started by supplying the reaction tube with pentachloroacetone that had previously been vaporized, at a flow rate of 36 g/hr. Pentachloroacetone in a total amount of 230 g was supplied to the reaction tube. The reaction products (gas) released from the reaction tube were collected by a trap cooled in dry ice and acetone. With this, 130 g of an organic matter was obtained. By analysis with a gas chromatograph, it was found that this organic matter contains 39.9 wt % of 3,3-dichloro-1,1,1-trifluoroacetone, 18.7 wt % of 1,3,3-trichloro-1,1-difluoroacetone, and 10.3 wt % of 3-chloro-1,1,1-trifluoroacetone.

EXAMPLE 3

In this example, the reaction (fluorination) was conducted in the same manner as that of Example 2 by supplying the reaction tube with pentachloroacetone at a flow rate of 36 g/hr. The reaction products (gas) released from the reaction tube were allowed-to flow through sodium fluoride pellets and then analyzed with a gas chromatograph. When the content of 3,3-dichloro-1,1,1-trifluoroacetone in the reaction products was found to be less than 30 wt % by this analysis, the supply of pentachloroacetone to the reaction tube was stopped. Then, only hydrogen fluoride and nitrogen gases were allowed to flow through the reaction tube for 1 hr. After that, the supply of hydrogen fluoride and nitrogen gases thereto was stopped. Then, the reaction tube temperature was increased to 390° C., while air was allowed to flow through the reaction tube at a rate of 400 liter/hr. This condition was maintained for 8 hr. Then, the reaction tube temperature was decreased to 250° C., and hydrogen fluoride gas was allowed to flow therethrough at a flow rate of about 36 g/hr, together with nitrogen gas at a flow rate of about 1.2 liter/hr. Under this condition, the reaction tube temperature was increased to 300° C., and then maintained at this temperature for 1 hr. Then, the reaction tube temperature was decreased to 250° C., and then the reaction (fluorination) was started by supplying the reaction tube with pentachloroacetone that had previously been vaporized, at a flow rate of 36 g/hr, while nitrogen and hydrogen fluoride gases were allowed to flow through the reaction tube at flow rates of 1.2 liter/hr and 36 g/hr, respectively. Pentachloroacetone in a total amount of 593 g was supplied to the reaction tube. The reaction products (gas) released from the reaction tube were collected by a trap cooled in dry ice and acetone With this, 342 g of an organic matter was obtained. By analysis with a gas chromatograph, it was found that this organic matter contains 47.9 wt % of 3,3-dichloro-1,1,1-trifluoroacetone, 12.5 wt % of 1,3,3-trichloro-1,1-difluoroacetone, and 11.0 wt % of 3-chloro-1,1,1-trifluoroacetone.

EXAMPLE 4

In this example, the fluorination catalyst was prepared as follows. At first, 2.7 liter of a $CrCl_3$ aqueous solution was prepared by dissolving 896 g of $CrCl_3 6H_2O$ into pure water. Into this solution, there was immersed 400 g of the same granular activated alumina as that of Example 2, and then this solution was allowed to stand still for one day and one night. After that, the activated alumina was separated from the solution by filtration, and then was dried for one day and one night at 100° C. in a hot-air circulating type oven. The thus obtained chromium-carried alumina was put into a cylindrical reaction tube that was equipped with an electric furnace and was made of stainless steel (SUS316L) and had a diameter of 4.2 cm and an axial length of 60 cm. The reaction tube temperature was increased to 300° C., while nitrogen gas was allowed to flow therethrough. Then, at the time when a trace of water was not found in the exit gas, it was started to allow hydrogen fluoride to flow therethrough, together with nitrogen gas. Then, hydrogen fluoride concentration of the mixture of hydrogen fluoride and nitrogen was gradually increased. When a hot spot produced by fluorinating the chromium-carried alumina reached the end of exit of the reaction tube, the reaction tube temperature was further increased to 450° C. Then, this condition was maintained for 1 hr, thereby preparing the fluorination catalyst.

Then, the fluorination was conducted as follows. At first, a cylindrical reaction tube for conducting a gas phase reaction was charged with 400 g of the above-prepared fluorination catalyst. This reaction tube was equipped with an electric furnace and was made of stainless steel (SUS316L) and had a diameter of 4.2 cm and an axial length of 60 cm. Then, the reaction tube temperature was increased to 250° C., while nitrogen gas was allowed to flow therethrough at a flow rate of about 1.2 liter/hr. Then, hydrogen fluoride gas was also allowed to flow therethrough at a flow rate of about 36 g/hr, together with nitrogen gas. Then, the reaction tube temperature was increased to 300° C., and then this condition was maintained for 1 hr. Then, the reaction tube temperature was decreased to 260° C., and then the reaction (fluorination) was started by supplying the reaction tube with pentachloroacetone that had previously been vaporized, at a flow rate of 36 g/hr, with nitrogen gas at a flow rate of 1.2 liter/hr and with hydrogen fluoride at a flow rate of 36 g/hr. Pentachloroacetone in a total amount of 230 g was supplied to the reaction tube. The reaction products (gas) released from the reaction tube were collected by a trap cooled in dry ice and acetone. With this, 130 g of an organic matter was obtained. By analysis with a gas chromatograph, it was found that this organic matter contains 34.0 wt % of 3,3-dichloro-1,1,1-trifluoroacetone, 9.7 wt % of 1,3,3-trichloro-1,1-difluoroacetone, and 14.5 wt % of 3-chloro-1,1,1-trifluoroacetone.

EXAMPLE 5

In this example, the fluorination catalyst was prepared as follows. At first, 500 ml of a $Fe(NO_3)_3$ aqueous solution was prepared by dissolving 145 g of $Fe(NO_3)_3 6H_2O$ into pure water. Into this solution, there was immersed 500 g of a fluorinated alumina prepared by the same treatment as that of Example 2, and then this solution was allowed to stand still for one day and one night, After that, the fluorinated alumina was separated from the solution by filtration, and then was dried for one day and one night at 100° C. in a hot-air circulating type oven. The thus obtained iron-carried fluorinated alumina was put into a cylindrical reaction tube that was the same as that of Example 4. The reaction tube temperature was increased to 300° C., while nitrogen gas was allowed to flow therethrough. Then, at the time when a trace of water was slot found in the exit gas, it was started to allow hydrogen fluoride to flow therethrough, together with nitrogen gas. Then, hydrogen fluoride concentration of the mixture of hydrogen fluoride and nitrogen was gradually increased. When a hot spot produced by fluorinating the iron-carried fluorinated alumina reached the end of exit of the reaction tube, this condition was maintained for 1 hr, thereby preparing the fluorination catalyst.

Then, the fluorination was conducted as follows. At first, a cylindrical reaction tube for conducting a gas phase reaction that was the same as that of Example 4 was charged with 400 g of the above-prepared fluorination catalyst. Then, the reaction tube temperature was increased to 250° C., while nitrogen gas was allowed to flow therethrough at a flow rate of about 1.2 liter/hr. Then, hydrogen fluoride gas was also allowed to flow therethrough at a flow rate of about 36 g/hr, together with nitrogen gas. Then, the reaction tube temperature was increased to 300° C., and then this condition was maintained for 1 hr. Then, the reaction tube temperature was decreased to 280° C., and then the reaction (fluorination) was started by supplying the reaction tube with pentachloroacetone that had previously been vaporized, at a flow rate of 36 g/hr, with nitrogen gas at a flow rate of 1.2 liter/hr and with hydrogen fluoride at a flow rate of 36 g/hr. Pentachloroacetone in a total amount of 230 g was supplied to the reaction tube. The reaction products (gas) released from the reaction tube were collected by a trap cooled in dry ice and acetone. With this, 125 g of an organic matter was obtained. By analysis with a gas chromatograph, it was found that this organic matter contains 55.0 wt % of 3,3-dichloro-1,1,1-trifluoroacetone, 5.3 wt % of 3,3,3-trichloro-1,1,1-trifluoroacetone, and 17.3 wt % of 3-chloro-1,1,1-trifluoroacetone.

The following nonlimiting Example 6 is illustrative of the second aspect of the present invention.

EXAMPLE 6

At first, the fluorination catalyst was prepared in the same manner as that of Example 2. Then, a cylindrical reaction tube that was the same as that of Example 2 was charged with 400 g of the obtained fluorination catalyst. Then, the same operations as those of Example 2 were conducted until the reaction (fluorination) was started by supplying the reaction tube with pentachloroacetone that had previously been vaporized, at a flow rate of 36 g/hr. While pentachloroacetone was supplied to the reaction tube during the reaction, the reaction products (gas) released from the reaction tube were collected by a trap cooled in dry ice and acetone. When the total amount of pentachloroacetone supplied to the reaction tube became 400 g, the supply of pentachloroacetone thereto was stopped. Then, only hydrogen fluoride and nitrogen gases were allowed to flow through the reaction tube for 1 hr. Then, the reaction tube temperature was increased to 390° C., while air was allowed to flow through the reaction tube at a rate of 400 liter/hr. This condition was maintained for 8 hr. Then, the reaction tube temperature was decreased to 250° C., and hydrogen fluoride gas was allowed to flow therethrough at a flow rate of about 36 g/hr, together with nitrogen gas at a flow rate of about 1.2 liter/hr. Under this condition, the reaction tube temperature was increased to 300° C., and then maintained at this temperature for 1 hr. Then, the reaction tube temperature was decreased to 250° C., and then the reaction (fluorination) was resumed by supplying the reaction tube with pentachloroacetone that had previously been vaporized, at a flow rate of 36 g/hr, while nitrogen and hydrogen fluoride gases were allowed to flow through the reaction tube at flow rates of 1.2 liter/hr and 36 g/hr, respectively. While pentachloroacetone was supplied to the reaction tube during the reaction, the reaction products (gas) released from the reaction tube were collected by a trap cooled in dry ice and acetone When the total amount of pentachloroacetone supplied to the reaction tube became 600 g after resumption of the reaction, the supply of pentachloroacetone thereto was stopped. Then, only hydrogen fluoride and nitrogen gases were allowed to flow through the reaction tube for 1 hr. Then, the reaction tube temperature was increased to 390° C. while air was allowed to flow through the reaction tube at a rate of 400 liter/hr. This condition was maintained for 8 hr. Then, the reaction tube temperature was decreased to 250° C., and hydrogen fluoride gas was allowed to flow therethrough at a flow rate of about 36 g/hr, together with nitrogen gas at a flow rate of about 1.2 liter/hr. Under this condition, the reaction tube temperature was increased to 300° C., and then maintained at this temperature for 1 hr. Then, the reaction tube temperature was decreased to 250° C., and then the reaction (fluorination) was resumed by supplying the reaction tube with pentachloroacetone that had previously been vaporized, at a flow rate of 36 g/hr, while nitrogen and hydrogen fluoride gases were allowed to flow through the reaction tube at flow rates of 1.2 liter/hr and 36 g/hr, respectively. While pentachloroacetone was supplied to the reaction tube during the reaction, the reaction products (gas) released from the reaction tube were collected by a trap cooled in dry ice and acetone. When the total amount of pentachloroacetone supplied to the reaction tube became 600 g after resumption of the reaction, the supply of pentachloroacetone thereto was stopped. The total of a recovered organic matter was in an amount of 928 g. By analysis with a gas chromatograph, it was found that this organic matter contains 46.2 wt % of 3,3-dichloro-1,1,1-trifluoroacetone, 11.3 wt % of 1,3,3-trichloro-1,1,1-difluoroacetone, 10.7 wt % of 3-chloro-1,1,1-trifluoroacetone, and 8.6 wt % of 3,3,3-trichloro-1,1,1-trifluoroacetone.

The obtained organic matter in an amount of 928 g was subjected to a simple distillation (preliminary distillation). With this, there was obtained 568 g of an effluent that was in the form of liquid and had a boiling point of from about 70 to 80° C. By analysis with a gas chromatograph, it was found that this effluent contains 70.4 wt % of 3,3-dichloro-1,1,1-trifluoroacetone, 21.7 wt % of 3-chloro-1,1,1-trifluoroacetone, and 5.9 wt % of 3,3,3-trichloro-1,1,1-trifluoroacetone.

Then, a distillation still equipped with a reflux tower having a diameter of 22 mm and an axial length of 270 mm and previously packed with a stainless steel packing, HELI-PACK No. 1 (1.5×2 mm), a trade name of Tokyo Tokushu Kana-ami Co., was charged with 35 g of water and 202 g of the effluent obtained by the preliminary distillation. When the distillation still was heated, reflux has started. Then, 149 g of a main effluent was obtained at 103.5° C. after obtaining effluents at about 70° C. and about 85° C. Then, the same volume of concentrated sulfuric acid was added to this main effluent, and the resultant mixture was vigorously shaken to remove water therefrom at room temperature. After that, the mixture separated into an upper organic layer and a lower water layer. The upper organic layer was found to be in an amount of 125.0 g and contain by analysis with a gas chromatograph 96.3 wt % of 3,3-dichloro-1,1,1-trifluoroacetone, 0.8 wt % of 3-chloro-1,1-trifluoroacetone, and 2.6 wt % of 3,3,3-trichloro-1,1,1-trifluoroacetone. The upper organic layer after the water removal was analyzed with respect to $^1$H-NMR and $^{13}$C-NMR, and the results are as follows.

| | | |
|---|---|---|
| $^1$H-NMR | CHCl$_2$ | 6.35 (s) |
| | C(OH)$_2$ | — |
| H$_2$O | — | |
| $^{13}$C-NMR | CF$_3$ | 115.05 (q, 292 Hz) |

-continued

| | | |
|---|---|---|
| | CO | 178.27 (q, 37.1 Hz) |
| | C(OH)$_2$ | — |
| | CHCl$_2$ | 63.88 (s) |

The above main effluent before the water removal was also analyzed with respect to $^3$H-NMR and $^{13}$C-NMR, and the results are as follows.

| | | |
|---|---|---|
| $^1$H-NMR | CHCl$_2$ | 5.92 (s) |
| | C(OH)$_2$ | 4.20 (bs) |
| | H$_2$O | 1.80 (bs) |
| $^{13}$C-NMR | CF$_3$ | 121.68 (q, 288 Hz) |
| | CO | — |
| | C(OH)$_2$ | 93.44 (q, 31.1 Hz) |
| | CHCl$_2$ | 71.65 (s) |

In this Comparative Example, water was omitted in the distillation, in contrast with Example 5. In fact, a distillation apparatus that was the same as that of Example 5 was charged with 326 g of the effluent obtained by the preliminary distillation of Example 5. When the distillation still was heated, reflux has started. Then, 56.5 g of a main effluent was obtained at about 75° C. after obtaining effluents at about 70° C. By analysis with a gas chromatograph, it was found that this main effluent contains 91.0 wt % of 3,3-dichloro-1,1,1-trifluoroacetone, 4.9 wt % of 3-chloro-1,1,1-trifluoroacetone, and 4.7 wt % of 3,3,3-trichloro 1,1,1-trifluoroacetone.

The entire disclosure of each of Japanese Patent Application Nos. 9-97623 filed on Apr. 15, 1997, 9-97624 filed on Apr. 15, 1997, and 9-137376 filed on May 28, 1997, including specification, claims, and summary, is incorporated herein by reference in its entirety.

What is claimed is:

1. A method for producing 3,3-dichloro-1,1,1-trifluoroacetone, with a selectivity of at least about 34%, fluorinating pentachloroacetone by hydrogen fluoride in the presence of a fluorination catalyst.

2. A method according to claim 1, wherein the step is conducted in a liquid phase in the presence of said fluorination catalyst that is an antimony compound.

3. A method according to claim 2, wherein said antimony compound is at least one compound selected from the group consisting of antimony pentachloride, antimony pentabromide, antimony pentaiodide, antimony pentafluoride, antimony trichloride, antimony tribromide, antimony triiodide, and antimony trifluoride.

4. A method according to claim 3, wherein said antimony compound is at least one of antimony pentachloride and antimony trichloride.

5. A method according to claim 2, wherein said antimony compound is in an amount of from 0.1 to 50 moles per 100 moles of said pentachloroacetone.

6. A method according to claim 2, wherein said step is conducted at a temperature of from 30 to 200° C. under a pressure of from 1.0 to 100.0 kg/cm$^2$.

7. A method according to claim 2, wherein said hydrogen fluoride is in an amount of from 3 to 50 moles per mol of said pentachloroacetone.

8. A method according to claim 2, wherein said step is conducted in the presence of a solvent which is at least one of 1,3-bistrifluoromethylbenzene and 2,4-dichloro-1-trifluoromethylbenzene.

9. A method according to claim 1, wherein the step is conducted in a gas phase in the presence of said fluorination catalyst.

10. A method according to claim 9, wherein said fluorination catalyst is a fluorinated alumina.

11. A method according to claim 9, wherein said fluorination catalyst is at least one compound of at least one metal selected from the group consisting of aluminum, chromium, manganese, nickel, cobalt, and iron.

12. A method according to claim 11, wherein said at least one compound is selected from the group consisting of oxides, fluorides, chlorides, fluorochlorides, oxyfluorides, oxychlorides, and oxyfluorochlorides.

13. A method according to claim 11, wherein said at least one compound is carried on a carrier.

14. A method according to claim 13, wherein said carrier is at least one selected from the group consisting of aluminum oxides, aluminum fluorides, aluminum chlorides, aluminum fluorochlorides, aluminum oxyfluorides, aluminum oxychlorides, aluminum oxyfluorochlorides, and activated carbon.

15. A method according to claim 13, wherein said at least one compound is in an amount of from 0.1 to 100 parts by weight per 100 parts by weight of said carrier.

16. A method according to claim 9, wherein said step is conducted at a temperature of from 150 to 500° C.

17. A method according to claim 9, wherein, prior to said step, the fluorination catalyst is treated with a fluorine-containing compound at a temperature that is not lower than a reaction temperature of said step.

18. A method according to claim 17, wherein said fluorine-containing compound is at least one compound selected from the group consisting of hydrogen fluoride, fluorohydrocarbons, and fluorochlorohydrocarbons.

19. A method according to claim 9, wherein a molar ratio of said pentachloroacetone to said hydrogen fluoride is from 1:50 to 1:3.

20. A method according to claim 9, wherein said step is conducted under a pressure of from 1 to 10 kg/cm$^2$.

21. A method according to claim 1, wherein a crude 3,3-dichloro-1,1,1-trifluoroacetone produced by said step is purified by a distillation in the presence of water, thereby to produce 3,3-dichloro-1,1,1-trifluoroacetone which is substantially free of organic matters other than 3,3-dichloro-1,1,1-trifluoroacetone.

22. A method according to claim 21, wherein said water is in an amount of from 2 to 5 moles per mol of 3,3-dichloro-1,1,1-trifluoroacetone contained in said crude 3,3-dichloro-1,1,1-trifluoroacetone.

23. A method according to claim 21, wherein said crude 3,3-dichloro-1,1,1-trifluoroacetone comprises a first impurity that is at least one of 3-chloro- 1,1,1-trifluoroacetone and 3,3,3-trichloro-1,1,1-trifluoroacetone, said first impurity being removed from said crude 3,3-dichloro-1,1,1-trifluoroacetone by said distillation.

24. A method according to claim 23, wherein, prior to said distillation, said crude 3,3-dichloro-1,1,1-trifluoroacetone is subjected to a preliminary distillation, thereby to remove from said crude 3,3-dichloro-1,1,1trifluoroacetone a second impurity that is different from said first impurity.

25. A method according to claim 24, wherein said second impurity is a chlorofluoroacetone having five halogen atoms and one hydrogen atom in the molecule.

26. A method for producing 3,3-dichloro-1,1,1-trifluoroacetone, said method comprising a step of purifying a crude 3,3-dichloro-1,1,1-trifluoroacetone by a distillation in the presence of water, thereby to produce 3,3-dichloro-1,1,1-trifluoroacetone which is substantially free of organic matters other than said 3,3-dichloro-1,1,1-trifluoroacetone.

27. A method according to claim 26, wherein said 3,3-dichloro-1,1,1-trifluoroacetone is recovered as an effluent having a boiling point of from 103 to 105° C. under a pressure of about 1 kg/cm².

28. A method according to claim 26, wherein said water is in an amount of from 2 to 6 moles per mol of 3,3-dichloro-1,1,1-trifluoroacetone contained in said crude 3,3-dichloro-1,1,1-trifluoroacetone.

29. A method according to claim 26, wherein said crude 3,3-dichloro-1,1,1-trifluoroacetone comprises a first impurity that is at least one of 3-chloro-1,1,1-trifluoroacetone and 3,3,3-trichloro-1,1,1-trifluoroacetone, said first impurity being removed from said crude 3,3-dichloro-1,1,1-trifluoroacetone by said distillation.

30. A method according to claim 29, wherein, prior to said distillation, said crude 3,3-dichloro-1,1,1-trifluoroacetone is subjected to a preliminary distillation, thereby to remove from said crude 3,3-dichloro-1,1,1-trifluoroacetone a second impurity that is different from said first impurity.

31. A method according to claim 30, wherein said second impurity is a chlorofluoroacetone having five halogen atoms and one hydrogen atom in the molecule.

* * * * *